US009033861B2

(12) United States Patent
Fischell et al.

(10) Patent No.: US 9,033,861 B2
(45) Date of Patent: May 19, 2015

(54) LOW FREQUENCY NEUROSTIMULATOR FOR THE TREATMENT OF NEUROLOGICAL DISORDERS

(75) Inventors: David R. Fischell, Fair Haven, NJ (US); Adrian R.M. Upton, Dundas (CA)

(73) Assignee: NeuroPace, Inc., Mountain View, CA (US)

(*) Notice: Subject to any disclaimer, the term of this patent is extended or adjusted under 35 U.S.C. 154(b) by 1452 days.

(21) Appl. No.: 12/549,303

(22) Filed: Aug. 27, 2009

(65) Prior Publication Data

US 2009/0318747 A1 Dec. 24, 2009

Related U.S. Application Data

(60) Continuation of application No. 11/436,676, filed on May 16, 2006, now Pat. No. 7,601,116, which is a continuation of application No. 10/245,992, filed on Sep. 17, 2002, now abandoned, which is a division of application No. 09/652,964, filed on Aug. 31, 2000, now Pat. No. 6,591,138.

(51) Int. Cl.
| | |
|---|---|
| *A61N 2/04* | (2006.01) |
| *A61N 1/36* | (2006.01) |
| *A61N 1/32* | (2006.01) |
| *A61N 2/00* | (2006.01) |
| *A61N 2/02* | (2006.01) |

(52) U.S. Cl.
CPC .............. *A61N 1/36021* (2013.01); *A61N 1/32* (2013.01); *A61N 1/36025* (2013.01); *A61N 1/36071* (2013.01); *A61N 1/36082* (2013.01); *A61N 2/006* (2013.01); *A61N 2/008* (2013.01); *A61N 2/02* (2013.01)

(58) Field of Classification Search
None
See application file for complete search history.

(56) References Cited

U.S. PATENT DOCUMENTS

| | | |
|---|---|---|
| 3,850,161 A | 11/1974 | Liss |
| 3,863,625 A | 2/1975 | Viglione et al. |
| 3,918,461 A | 11/1975 | Cooper |
| 4,019,518 A | 4/1977 | Maurer et al. |
| 4,305,402 A | 12/1981 | Katims |
| 4,373,527 A | 2/1983 | Fischell |
| 4,646,744 A | 3/1987 | Capel |
| 4,793,353 A | 12/1988 | Borkan |
| 4,844,075 A | 7/1989 | Liss et al. |
| 4,994,016 A | 2/1991 | Atwood |
| 5,084,007 A | 1/1992 | Malin et al. |
| 5,154,172 A | 10/1992 | Terry et al. |
| 5,169,380 A | 12/1992 | Brennan |
| 5,179,950 A | 1/1993 | Stanislaw |

(Continued)

OTHER PUBLICATIONS

Adamec, R.E., "Evidence that Limbic Neural Plasticity in the Right Hemisphere Mediates Partial Kindling Induced Lasting Increases in Anxiety-Like Behavior," Brain Research (1999); 839: pp. 133-152.

(Continued)

*Primary Examiner* — Kennedy Schaetzle
(74) *Attorney, Agent, or Firm* — Arent Fox LLP

(57) ABSTRACT

A system for treating neurological conditions by low-frequency time varying electrical stimulation includes an electrical device for applying such low-frequency energy, in a range below approximately 10 Hz, to the patient's brain tissue. An implantable embodiment applies direct electrical stimulation to electrodes implanted in or on the patient's brain, while a non-invasive embodiment causes a magnetic field to induce electrical currents in the patient's brain.

7 Claims, 5 Drawing Sheets

(56) References Cited

U.S. PATENT DOCUMENTS

| | | | |
|---|---|---|---|
| 5,186,170 A | 2/1993 | Varrichio et al. | |
| 5,188,104 A | 2/1993 | Wernicke et al. | |
| 5,215,086 A | 6/1993 | Terry et al. | |
| 5,231,988 A | 8/1993 | Wernicke et al. | |
| 5,263,480 A | 11/1993 | Wernicke et al. | |
| 5,269,303 A | 12/1993 | Wernicke et al. | |
| 5,299,569 A | 4/1994 | Wernicke et al. | |
| 5,330,515 A | 7/1994 | Rutecki et al. | |
| 5,335,657 A | 8/1994 | Terry et al. | |
| 5,342,410 A | 8/1994 | Braverman | |
| 5,421,817 A | 6/1995 | Liss et al. | |
| 5,540,734 A | 7/1996 | Zabara | |
| 5,571,150 A | 11/1996 | Wernicke et al. | |
| 5,683,422 A | 11/1997 | Rise | |
| 5,707,334 A | 1/1998 | Young | |
| 5,707,400 A | 1/1998 | Terry et al. | |
| 5,713,923 A | 2/1998 | Ward et al. | |
| 5,716,377 A | 2/1998 | Rise et al. | |
| 5,752,979 A | 5/1998 | Benabid | |
| 5,769,778 A | 6/1998 | Abrams et al. | |
| 5,782,798 A | 7/1998 | Rise | |
| 5,782,874 A | 7/1998 | Loos | |
| 5,792,186 A | 8/1998 | Rise | |
| 5,800,459 A | 9/1998 | Spano et al. | |
| 5,800,474 A | 9/1998 | Benabid et al. | |
| 5,833,709 A | 11/1998 | Rise et al. | |
| 5,938,688 A | 8/1999 | Schiff | |
| 5,975,085 A | 11/1999 | Rise | |
| 5,978,702 A | 11/1999 | Ward et al. | |
| 6,016,449 A | 1/2000 | Fischell et al. | |
| 6,058,331 A | 5/2000 | King | |
| 6,104,956 A | 8/2000 | Naritoku et al. | |
| 6,109,269 A | 8/2000 | Rise et al. | |
| 6,128,537 A | 10/2000 | Rise | |
| 6,128,538 A | 10/2000 | Fischell et al. | |
| 6,134,474 A | 10/2000 | Fischell et al. | |
| 6,402,678 B1 * | 6/2002 | Fischell et al. | 600/13 |
| 7,294,101 B2 * | 11/2007 | Fischell et al. | 600/13 |
| 7,407,478 B2 * | 8/2008 | Zangen et al. | 600/13 |
| 7,494,458 B2 * | 2/2009 | Fischell et al. | 600/13 |
| 7,601,116 B2 * | 10/2009 | Fischell et al. | 600/14 |

OTHER PUBLICATIONS

Agnew, W.F., et al., "Considerations for Safety in the Use of Extracranial Stimulation for Motor Evoked Potentials," Neurosurgery (1987) 20: pp. 143-147.

Aurora, S. K., et al., "Brain Excitability in Migraine: Evidence from Transcranial Magnetic Stimulation Studies," Current Opinion in Neurology (1998) 11: pp. 205-209.

Bartlett, J.R., et al., "Deleterious Effects of Prolonged Electrical Excitation of Striate Cortex in macaques," Brain Behav. Evol. (1977) 14: pp. 46-666.

Bridgers, S.L., "The Safety of Transcranial Magnetic Stimulation Reconsidered: Evidence Regarding Cognitive and Other Cerebral Effects," Magnetic Motor Stimulation: Basic Principles and Clinical Experience (1991) EEG Suppl. 43: pp. 170-179.

Buzsaki, G., et al., "Depth Profiles of Hippocampal Rhythmic Slow Activity ('theta rhythm') Depend on Behavior," Electroencephologr. Clin. Neurophysiol. (1985) 61: pp. 77-88.

Cain, D. P., et al., "Kindling with Low-Frequency Stimulation: Generality, Transfer and Recruiting Effects," Experimental Neurology (1981) 73: pp. 219-232.

Chen, R. et al., "Safety of Different Inter-Train Intervals for Repetitive Transcranial Magnetic Stimulation and Recommendations for Safe Ranges of Stimulation Parameters," Electroencephalograpy and Clinical Neurophysiology (1997) 105: pp. 415-421.

Classen, J. et al., "Epileptic Seizures Triggered Directly by Focal Transcranial Magnetic Stimulation," Electroencephalography and Clinical Neurophysiology (1995) 94: pp. 19-25.

Contreras, D., et al., "Cellular Basis of EEG Slow Rhythms: A Study of Dynamic Corticothalmic Relationships," J. Neurosci. (1995) 15: pp. 604-622.

Dennison, Z. et al., "Persistence of Kindling: Effect of Partial Kindling, Retention Interval, Kindling Site, and Stimulation Parameters," Epilepsy Research (1995) 21: pp. 171-182.

Dow, R.S., "Extrinsic Regulatory Mechanisms of Seizure Activity," Epilepsia (1965) 6: pp. 122-140.

Elger, C., et al., "Short Communication Seizure Prediction by Non-Linear Time Series Analysis of Brain Electrical Activity," European Journal of Neuroscience (1998) 10: pp. 786-789.

Emori, K., et al., "Changes in Paired-Pulse Depression During the Triggering of Seizures by 2 Hz Dentate Gyrus Stimulation: the Effect of the Kindling," Brain Research (1997) 776: pp. 250-254.

Ettinger, G.J., et al., "Experimentation with a Transcranial Magnetic Stimulation System for Functional Brain Mapping," Medical Image Analysis (1998) vol. 2, No. 2, pp. 133-142.

Fischer, R.S., et al., "Placebo-Controlled Pilot Study of CentromedianThalamic Stimulation in Treatment of Intractable Seizures," Epilepsia (1992) 33: pp. 841-851.

Gaito, J., et al., "Interference Effect of 3 Hz Brain Stimulation on Kindling Behavior Induced by 60 Hz Stimulation," Epilepsia (1980) 21: pp. 73-84.

Gaito, J., "The Effect of Variable Duration One Hertz Interference on Kindling," Le Journal Canadien des Sciences Neurologiques (1980): 7: pp. 59-64.

Gaito, J., et al., "The Effect of Low Frequency and Direct Current Stimulation on the Kindling Phenomenon in Rats," Le Journal Canadiens des Sciences Neurologiques (1981) 8(3): pp. 249-253.

Gaito, J., "Suppression of Kindling Behavior," J. Psychology (1984) 118: pp. 113-125.

Girvin, J.P., "Cerebral (Cortical) Biostimulation," PACE (1986) 9: pp. 764-771.

Goddard, G. V., et al., "A Permanent Change in Brain Function Resulting From Daily Electrical Stimulation," Experimental Neurology (1967) 25: pp. 295-330.

Goodman, J.H., "Experimental Models of Status Epilepticus," in S. L. Peterson et al., eds., Neuropharmacology Methods in Epilepsy Research, CRC Press (1998) pp. 95-125.

Gybels, J., et al., "Electrical Stimulation of the Central Gray for Pain Relief in Human: Autopsy Data," Acta Neurochirugica (1980) Suppl. 30: pp. 259-268.

Hallet, M., "Transcranial Magnetic Stimulation and the Human Brain," Nature (2000) 406: pp. 147-150.

Jennum, P., et al., "Transcranial Magnetic Stimulation. Its Role in the Evaluation of Patients with Partial Epilepsy," Acta Neurol. Scand. (1994) Suppl. 152: pp. 93-96.

Krauss, G. L., et al., "Cerebellar and Thalamic Stimulation for Epilepsy," in O. Devinsky et al., eds., Electrical and Magnetic Stimulation of the Brain and Spinal Cord, New York: Raven Press, Ltd. (1993) pp. 231-245.

Kreindler, A., "Active Arrest Mechanisms of Epileptic Seizures," Epilepsia (1962) 2: pp. 329-337.

Linden, D.J., "Long-Term Synaptic Depression in the Mammalian Brain," Neuron (1994) 12: pp. 457-472.

Leung, L.S., et al., "Theta-Frequency Resonance in Hippocampal CA1 Neurons in Vitro Demonstrated by Sinusoidal Current Injection," J. Neurophysiol. (1998) 79: pp. 1592-1596.

MacDonell, R.A.L., et al., "Motor Cortex Localization Using Functional MRI and Transcranial Magnetic Stimulation," Neurology (1999) 53: pp. 1462-1467.

Maertens De Noordhout, A., et al., "Transcranial Magnetic Stiulation in Migraine," Transcranial Magnetic Stimulation (1999) EEG Suppl. 51: pp. 260-264.

Migita, K., et al., "Transcranial Magnetic Coil Stimulation of Motor Cortex in Patients with Central Pain," Neurosurgery (1995) vol. 36, No. 5, pp. 1037-1040.

Minabe, Y. et al.,"Low-Frequency Kindling as a New Experimental Model of Epilepsy," Experimental Neurology (1986) 94: pp. 317-323.

Mortimer, J.T., et al., "Experimental Nondestructive Electrical Stimulation of the Brain and Spinal Cord," J. Neurosurg. (1970) 32: pp. 553-339.

Ojemann, G.A., et al., "Stereotactic and Other Procedures for Epilepsy," in D.P. Purpura et al., eds., Neurosurgical Management of the Epilepsies, Advances in Neurology (1975) 8: pp. 241-263.

(56) References Cited

OTHER PUBLICATIONS

Osorio, L., et al., "Real-Time Automated Dection and Quantitative Analysis of Seizures and Short-Term Prediction of Clinical Onset," Epilepsia (1998) 39: pp. 615-627.

Pascual-Leone, A., et al., "Akinesia in Parkinson's Disease," Neurology (1994) 44: pp. 884-891.

Psatta, D.M., "Control of Chronic Experimental Focal Epilepsy by Feedback Caudatum Stimulations," Epilepsia (1983) 24: pp. 444-454.

Pudenz, R.H., et al., "Electrical Stimulation of the Brain. II. Effects on the Blood-Brain Barrier," Surg. Neurol. (1975) 4: pp. 265-270.

Reimer, G. R., et al., "Effects of Cerebellar Stimulation on Cobalt-Induced Epilepsy in the Cat," Electroenceph. Clin. Neurophysiol. (1967) 23: pp. 456-462.

Rowland, V., et al., "The Production of Brain Lesions With Electric Currents," J. Neurosurg. (1960) 17: pp. 55-69.

Schmutz, M., "Relevance of Kindling and Related Processes to Human Epileptogenesis," Prog. Neuro-Psychopharmacolog. & Biol. Psychiat. (1987) 11: pp. 5050-5525.

Schulze-Bonhage, A., et al., "Safety of Single and Repetitive focal Transcranial Magnetic Stimuli as Assessed by Intracranial EEG Recordings in Patients with Partial Epilepsy," J. Neurol. (1999) 246: pp. 914-919.

Sramka, M., et al., "Observation of Kindling Phenomenon in Treatment of Pain by Stimulation in Thalamus," in W.H. Sweet et al., eds., Neurosurgical Treatment in Psychiatry, Pain and Epilepsy, Baltimore: University Park Press (1977) pp. 651-654.

Staton, R.D., et al., "The Electroencephalographic Pattern During Electroconvulsive Therapy: V. Observations on the Origin of Phase III Delta Energy and the Mechanism of Action of ECT," Clin. Electroencephalogr. (1988) 10: pp. 176-198.

Ullal, G.R., et al., "Low Frequency Stimulation Induces an Increase in After-Discharge Thresholds in Hippocampal and Amygdaloid Kindling," Epilepsy Res. 3 (1989) pp. 232-235.

Wang, H. et al., "LTD and LTP Induced by Transcranial Magnetic Stimulation in Auditory Cortex," Neuroreport (1996) 7: pp. 521-525.

Weiss et al., S.R.B., et al., "Quenching: Inhibition of Development and Expression of Amygdala Kindled Seizures with Low Frequency Stimulation," NeuroReport (1995) 6: pp. 2171-276.

Weiss et al., S.R. et al., "Quenching Revisited: Low Level Direct Current Inhibits Amygdala-Kindled Seizures," Experimental Neurology (1998) 154: pp. 185-192.

E.M. Wasserman, "Risk and Safety of Repetitive Transcranial Magnetic Stimulation: Report and Suggested Guidelines from the International Workshop on the Safety of Repetitive Transcranial Mag. Stim. . . . ," Electroenceph. and Clin Neurophys. 108 (1998), pp. 1-16.

J. Gaito et al., "The Effect of Several Intertrial Intervals on the 1 Hz Interference Effect," Le Journal Canadian des Sciences Neurologiques 1981; 8(1): pp. 61-65.

\* cited by examiner

LOW FREQUENCY NEUROSTIMULATOR FOR THE TREATMENT OF NEUROLOGICAL DISORDERS

CROSS-REFERENCE TO RELATED APPLICATIONS

This is a continuation of U.S. patent application Ser. No. 11/436,676, filed May 16, 2006, now U.S. Pat. No. 7,601,116, which is a continuation of U.S. patent application Ser. No. 10/245,992, filed Sep. 17, 2002, now abandoned, which was a divisional of U.S. patent application Ser. No. 09/652,964, filed Aug. 31, 2000, now U.S. Pat. No. 6,591,138.

BACKGROUND

1. Technical Field

This invention is in the field of devices for the treatment of neurological disorders in human subjects, particularly those disorders that originate in the brain.

2. Background

The current state of the art in treating neurological disorders such as epilepsy or Parkinson's disease involves either drugs, destructive nigral lesions or the open-loop electrical stimulation of neurological tissue. Drug therapy has been shown to have significant short and long-term side effects and is often ineffective. In U.S. Pat. No. 3,850,161, Liss describes a continuous closed-loop feedback system which will always feedback part of the brain EEG signal to separate electrodes so that if a large EEG signal occurs it will be fed back in an attempt to cancel out the original signal. The system does not take advantage of recently developed digital signal processing and microcomputer technology by which feedback signals can be activated only when a neurological event occurs, nor does it provide a practical way to recognize and intervene during early stages in the evolution of a neurological event. In addition, the Liss device is not programmable and it does not provide any capability to record EEG signals. Examples of a "neurological event" are the occurrence of an epileptic seizure, a tremor or the occurrence of a migraine aura or migraine headache. A "neurological event" is defined herein as either the precursor of an event such as an epileptic seizure, or the event itself. This concept of detecting an electrical precursor that is a first type of neurological event that occurs some time before the "real" event (i.e. anomalous brain electrical activity or a particular pattern of neural activity associated with clinical symptoms) is an important aspect of the present invention. It has been shown that both epileptic seizures and Parkinson's tremors have precursors that occur before and can be used to predict the onset of the clinical symptom. It is also very likely that other neurological events such as migraine headaches and depression would have anomalous electrical activity predictive of the onset of clinical symptoms. Methods for prediction of epileptic seizures have been published by Elger and Lehnertz (in Elger, C. E., and Lehnertz, K., "Seizure prediction by non-linear time series analysis of brain electrical activity," Eur. J. Neurosci. 1998 February; 10(2): 786-9, and Osorio, Frei and Wilkinson (in Osorio, I., et al., "Real-time automated detection and quantitative analysis of seizures and short-term prediction of clinical onset," Epilepsia 1998 June; 39(6): 615-27.

Maurer and Sorenson in U.S. Pat. No. 4,019,518 describe a combined internal/external system for electrical stimulation of the body with biphasic pulses but do not describe any means of detecting neurological events. Fischell in U.S. Pat. No. 4,373,527 describes a programmable medication infusion system but does not anticipate its use in response to a detected neurological event.

More recently, a device has been approved for human use to stimulate the vagus nerve in a continuous fashion with the objective of decreasing the rate of epileptic seizures. Clinical reports on such devices indicate only a modest degree of success in that only 50% of the patients experience a greater than 20% reduction in the rate of epileptic seizures. Another device that has been recently introduced into clinical practice utilizes intermittent or continuous stimulation of the thalamus for the treatment of involuntary motion disorders such as Parkinson's syndrome. Neither of these two open-loop devices described above is highly effective for the treatment of a neurological disorder such as epilepsy, and neither anticipates the use of decision making in order to optimize a response to terminate the precursor of a neurological event or the neurological event itself; nor does either device allow for the recording of EEG signals. In addition, both known devices use stimulation frequencies above 10 Hz, which for the reasons set forth in detail below, are not optimal.

Fischell et al in U.S. Pat. No. 6,016,449, which is incorporated herein by reference, teaches a fully implantable neurostimulator capable of responsive treatment of neurological disorders. However, Fischell does not discuss in detail the advantageous use of low frequency stimulation as a means of inhibiting epiliptiform activity.

It is well known that slow wave potentials in the brain are often inhibitory in nature yet all known stimulation attempts to treat epilepsy in humans have used relatively high frequency stimulation, in most cases greater than 20 Hz. These higher frequencies, while effective for a brain mapping type procedure, have significant potential to induce epileptogenic activity. In fact, Hallett in "Transcranial magnetic stimulation and the human brain," Nature, Vol. 406, 13 Jul. 2000, states that while "rapid repetitive transcranial magnetic stimulation (rTMS), at frequencies of 5 Hz and higher, will transiently enhance motor excitability . . . slow rTMS, at 1 Hz will transiently depress excitability."

SUMMARY

There is good evidence that slow wave activity is inhibitory in the central nervous system of man (Staton, R. D. et al., "The electroencephalographic pattern during electroconvulsive therapy: V. Observations on the origins of phase III delta energy and the mechanism of action of ECT," Clin. Electroencephalogr. 1988 October; 19(4): 176-198 and animals (Buzsaki, G. et al., "Depth profiles of hippocampal rhythmic slow activity ('theta rhythm') depend on behaviour," Electroencephalogr. Clin. Neurophysiol. 1985 July; 61(1): 77-78) including such stimulation applied to the hippocampus (Leung, L. S. et al., "Theta-frequency resonance in hippocampal CA1 neurons in vitro demonstrated by sinusoidal current injection," J. Neurophysiol. 1998 March; 79(3): 1592-6). These slow waves may be at theta frequencies (4 to 7 Hz—Buzsaki et al. 1985), delta frequencies (1 to 3 Hz—Staton et al. 1988), or even at less then 1 Hz (Contreras, D. et al., "Cellular basis of EEG slow rhythms: a study of dynamic corticothalamic relationships," J. Neurosci. 1995 January; 15(1 Pt 2): 604-22). Paatta et al. (in "Control of chronic experimental focal epilepsy by feedback caudatum stimulation," Epilepsia 1983 August; 24(4): 444-54) describe successful ictal spike depression by 5 Hz stimulation of the caudate nucleus (CN) in cat brains. The article also states that stimulation of the thalamus, mesencephalic reticular formation or hypothalamus was not effective. Finally, Hallett (in "Transcranial magnetic stimulation and the human brain," Nature 2000; 406 (July 13): 147-150) discusses the inhibitory effects of low frequency pulsing from a transcranial magnetic stimulator.

The present invention includes transcranial stimulation, or direct brain stimulation from multiple electrodes, in either an open or closed-loop system for the treatment of certain neurological disorders such as epilepsy, migraine headaches and Parkinson's disease. A purpose of the present invention is to overcome the shortcomings of all known devices for the treatment of such disorders. Specifically, the present invention utilizes slow wave potentials (low frequency stimulation in a range of approximately 1 to 10 Hz) to prevent or abort a neurological event.

One embodiment of the present invention envisions a multiplicity of brain electrodes placed either within the brain, on the surface of the brain itself, or on the dura mater that surrounds the brain. Some or all of these brain electrodes may be used to directly detect an abnormal neurological event such as an epileptic seizure, or they may be used to detect a pattern of electrical activity that precedes or accompanies an abnormal neurological event. A stimulation signal can also be applied to any one, several, or all elements of such an electrode array. The stimulation signals sent to each electrode may be identical or they may be programmed to differ in amplitude, frequency, waveform, phase and time duration. It is also envisioned that sensing electrodes may be entirely separate from the electrodes used for responsive stimulation.

It is also envisioned that appropriate selection (i.e., location) of electrode sites can be used to enhance the reliability for detection and termination of a neurological event. Thus, the present invention envisions enhancement of detection by the use of the spatial domain as it applies to the positioning of detection and treatment electrodes.

A specific capability of this system is to provide electrical stimulation to a specific portion of the brain as the means of stopping a neurological event. It is believed that the earliest possible detection of a seizure and treatment of aberrant electrical activity from an epileptic focus has the highest probability of aborting the occurrence of a full seizure. It is envisioned that either through specific placement of treatment electrodes or by adjusting the phase of signals applied to an array of electrodes, stimulation can be directed to the locations(s) within the brain that offer the highest probability of stopping the seizure. Detection of an abnormal neurological event would allow detection of specific but apparently normal patterns of electrical activity, which are reliable producers of the abnormal event; stimulation during the appearance of such patterns may prevent the occurrence of the event.

A novel aspect of a preferred embodiment of this invention is that the entire implantable portion of this system for treating neurological disorders is implanted under the patient's scalp or intracranially. Such placement will either have the device located between the scalp and the cranium or within a hole in the cranium. Because of size constraints, the intracranial location is the preferred embodiment.

The implantable portion of the system includes: (1) electrodes that lie in close proximity to or actually within the brain, (2) a control module that contains a battery and all the electronics for sensing, recording and controlling brain activity, (3) electrically conducting wires that connect the control module to the electrodes, (4) a buzzer providing an acoustic signal or electrical "tickle" indicating that a neurological event has been detected, and (5) an input-output wire coil (or antenna) used for communication of the implanted system with any and all external equipment. The battery that provides power for the system and an electronics module are both contained within a metal shell that lies, in one embodiment, under the patient's scalp. The metal shell, which contains the electronics module and the battery collectively, forms the control module.

All electrodes connect by way of electrically conducting wires to electrical terminals that are formed into the metal shell. The electronics module is electrically joined to the brain electrodes by way of the shell's electrical terminals, which are electrically joined to the wires that connect to the brain electrodes.

An important aspect of the preferred embodiment of this device is the fact that the shell containing the electronics module and the battery, i.e. the control module, is to be placed in the cranium of the skull at a place where a significant volume of bone is removed. By placing the entire system within the cranium, (as opposed to having some wires extending into or through the patient's neck to a control module in the chest) the probability of wire breakage due to repeated wire bending is significantly reduced. However, the present invention also envisions the placement in the chest or abdomen of a control module if a large battery or a large volume electronics module dictates such a large size for the control module that it cannot be conveniently placed within the cranium. Such a thoracic or abdominal placement of a control module would typically require wires to be run through the patient's neck.

The present invention also envisions the utilization of an intracranial system for the treatment of certain diseases without placing wires through the neck. Specifically, an alternative embodiment of the invention envisions the use of electrodes in or on the brain with an intracranial control module used in conjunction with a remote sensor/actuator device implanted elsewhere in the patient's body. For example, blood pressure could be sensed with a threshold or, for example, 150 mm Hg, and if that pressure is exceeded, a signal transmitted by electrical conduction through the body from the remote sensor/actuator device could be received at the control module, which would initiate brain stimulation in such a way as to reduce the blood pressure. Conversely, if the brain perceives pain and generates a corresponding signal detectable by the intracranial control module, a signal could be sent by electrical conduction through the body to the remote sensor/actuator device, which would provide responsive electrical stimulation to locally stimulate a nerve, thereby reducing the perception of that pain. In still another embodiment, if a precursor of an epileptic seizure is detected, the remote sensor/actuator could be used to electrically stimulate one or both vagus nerves so as to stop the epileptic seizure from occurring. Such a remote device could be located in the trunk of the patient's body. In an embodiment of the invention, a remote sensor/actuator may be used to deliver instantaneous, intravenous, intraperitoneal, subdural or intraventricular (of the brain) therapeutic chemicals, including medication, neurotransmitters and ionic substances, alone or in conjunction with electrical stimulation. Such a remote sensor/actuator is disclosed in the above referenced U.S. Pat. No. 6,016,449 by Fischell et al.

It is also envisioned the ideal stimulation to prevent or abort a neurological event has a low frequency (e.g., 1 to 8 Hz) that would resemble slow wave inhibitory potentials and be significantly less likely to induce epileptiform activity. In one embodiment of the invention, the stimulation waveform is substantially sinusoidal and has minimal higher-order harmonics, and hence little energy above the fundamental frequency. In an alternative embodiment, the low frequency stimulation comprises a sequence of short duration biphasic pulses having a repetition rate of less than about ten pulses per second (10 Hz). Such stimulation could be applied to the caudate nucleus or other structures of the brain, including the hippocampus. As patients suffering from Parkinson's have an extremely low incidence of epilepsy and one manifestation of Parkinson's is characterized by a 5 Hz electrical oscillation that begins in the Thalamus, it is conceived that low frequency stimulation of the Thalamus could, in fact, be inhibitory to epileptiform activity. Such stimulation could be responsive to the detection of a precursor to a clinical seizure or the epileptiform activity from the seizure itself. Alternately, periodic slow wave stimulation applied without detection could prevent the brain from generating seizure activity. Although epilepsy is currently believed to be the most applicable use of such slow wave stimulation, it could also be successful for migraines, pain, tremor, Parkinson's, depression or other neurological disorders.

It is also envisioned that while the standard treatment would have a constant amplitude for the duration of the low frequency stimulation, it may be advantageous to have the amplitude begin high and decrease over the duration, begin low and increase over the duration, or vary according to any desired treatment plan. The typical duration of low frequency stimulation that would be used to stop a neurological event would be between 100 ms and 10 seconds.

Another embodiment of the present invention that would be significantly less invasive involves the use of Transcranial Magnetic Stimulation (TMS) from an external coil TMS stimulator. Such a device could be incorporated into a bicycle type helmet and could be used at the time a pre-event aura is sensed by the patient. Alternately, such an external system could be used in a repetitive or continuous mode for patients with serious disorders who often wear protective helmets. A TMS device could be extremely effective if it is pulsed on and off at frequencies below 10 Hz.

Thus it is an object of this invention to provide appropriate slow wave stimulation of the human brain in response to a detected neurological event in order to cause the cessation of that neurological event. The pattern and frequency of stimulation can be modified to provide optimal control of the unwanted neurological event in each patient.

Another object of this invention is to use periodic slow wave stimulation of the brain to treat neurological disorders.

Another object of the invention is to use continuous slow wave stimulation of the brain to treat neurological disorders.

Still another object of this invention is to have a system of electrodes connected by wires to a control module, the entire system being placed under the scalp or intracranially, and being substantially contained within an opening in the cranium.

Still another object of this system is to have essentially no flexure of interconnecting wires so as to enhance system reliability.

These and other objects and advantages of this invention will become apparent to a person of ordinary skill in this art upon careful reading of the detailed description of this invention including the drawings as presented herein.

DETAILED DESCRIPTION

Figure 1:
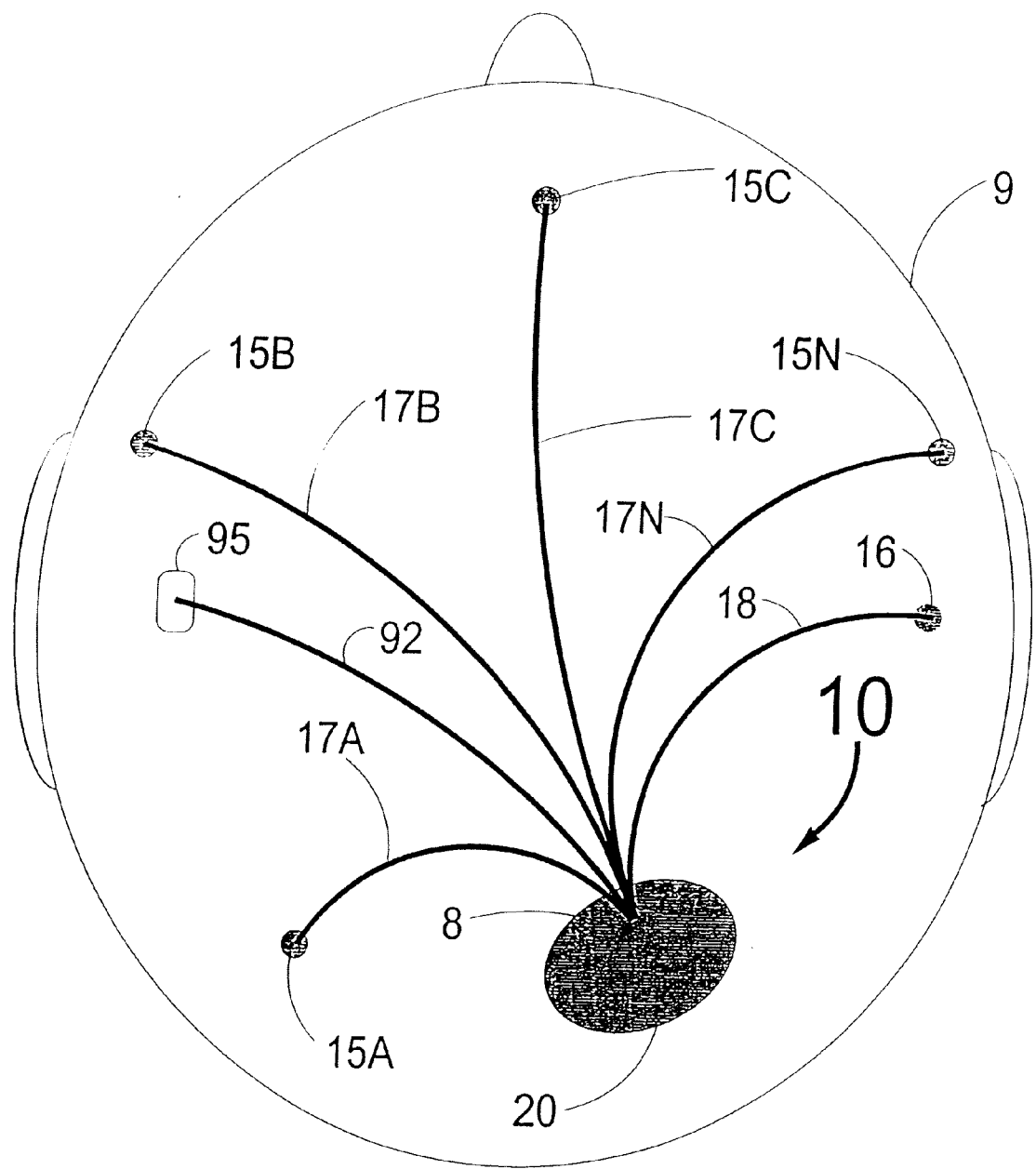
FIG. 1 is a top view of a human head showing the configuration of an implantable system for the treatment of neurological disorders as it would be situated in the human skull.

FIG. 1 illustrates the configuration of an implantable system 10 for the treatment of neurological disorders as it would be situated under the scalp of a human head 9, the system including a control module 20, electrodes 15A, 15B, 15C, 15N and 16 with wires 17A, 17B, 17C, 17N and 18 connected through a connector 8 to the control module 20. It is envisioned that the control module 20 is permanently implanted into the top of the patient's skull in a location where the skull is fairly thick. It is also envisioned that the control module 20 could be located in the trunk of the patient's body like a heart pacemaker with the connecting wires being run through the patient's neck, under the patient's skin or otherwise. Each of the electrodes 15A, 15B, 15C, 15N and 16 would be placed under the cranium and above the dura mater (i.e., placed epidurally) or placed deep into the brain. The connecting wires 17A, 17B, 17C, 17N and 18 would be run from the control module 20 underneath the scalp and then be connected to the electrodes placed beneath the patient's cranium. Although FIG. 1 shows only four active electrodes 15A, 15B, 15C, 15N with connecting wires 17A, 17B, 17C, 17N, more than four active electrodes with connecting wires may be used with the present invention. The electrode 16 (having the connecting wire 18) could be considered a common or indifferent electrode.

Throughout the detailed description of the present invention, the terminology "the electrodes 15A through 15N" is meant to include all electrodes 15A, 15B, 15C, . . . to 15N, inclusive, where N may be any integer greater than or equal to 1. Similar terminology using the words "through" or "to" for other groups of objects (i.e., wires 17A through 17N) will have a similar inclusive meaning.

Throughout FIGS. 1 through 25, inclusive, lines connecting boxes on block diagrams or on software flow charts will each be labeled with an element number. Lines without arrows between boxes or other elements shall indicate a single wire.

Lines with arrows connecting boxes or other elements are used to represent any of the following:

1. A physical connection, namely a wire or group of wires (data bus) over which analog or digital signals may be sent.

2. A data stream sent from one hardware element to another. Data streams include messages, analog or digital signals, commands, EEG information, and software downloads to change system operation and parameters.

3. A transfer of information between software modules. Such transfers include software subroutine calls with and without the passing of parameters, and the reading and writing of memory locations.

In each case, the descriptive text herein will indicate each specific use of a line with an arrow.

Figure 2:
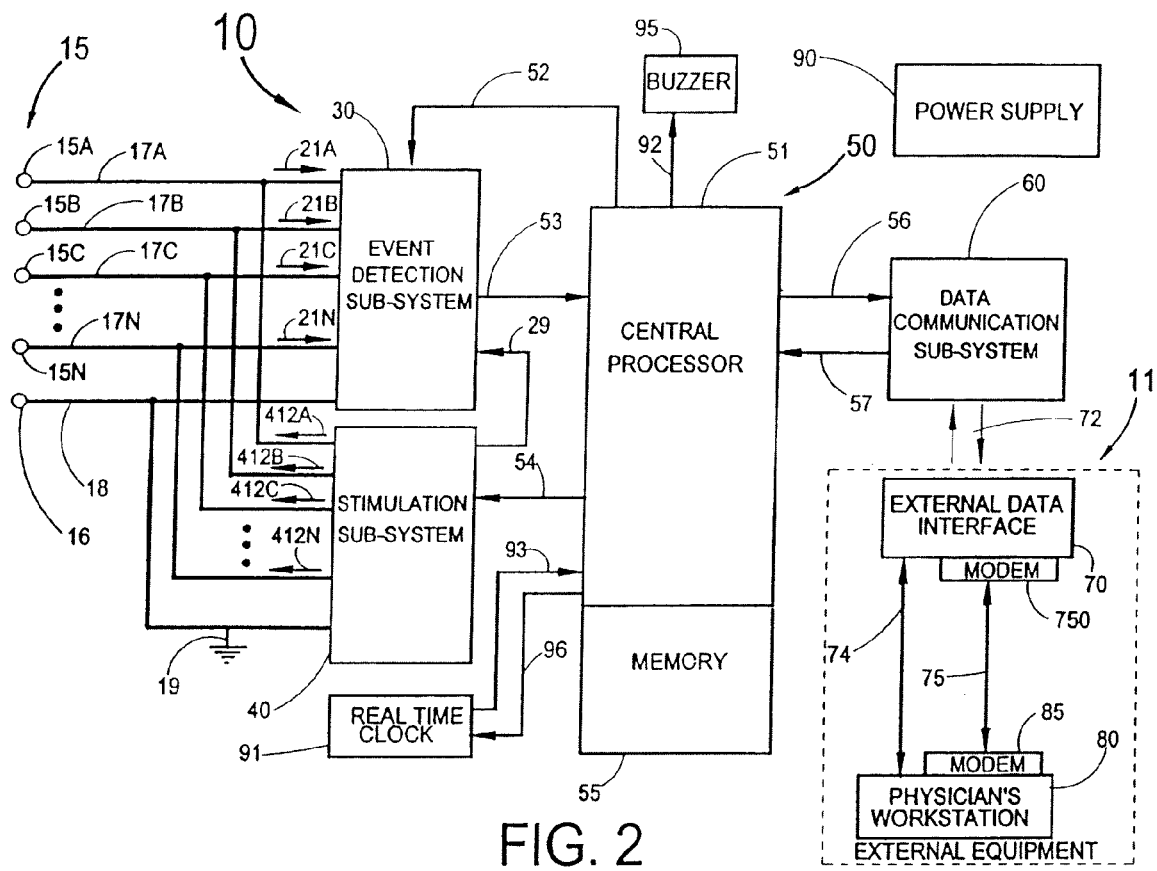
FIG. 2 is a block diagram of the implanted and external portions of the system.

FIG. 2 is a block diagram of the implantable system 10 and the external equipment 11. The wires 17A through 17N from the electrodes 15A through 15N, and the wire 18 from the common electrode 16, are shown connected to both an event detection sub-system 30 and a stimulation sub-system 40. In one embodiment of the invention, it is also envisioned to use the case of the control module 20 of FIG. 1 as the common (or indifferent) electrode 16. The wires 17A through 17N carry EEG signals 21A through 21N from the electrodes 15A through 15N to the event detection sub-system 30. The electrodes 15A through 15N can be energized by the stimulation sub-system 40 via the wires 17A through 17N to electrically stimulate the patient's brain using the stimulation signals 412A through 412N respectively. Although the electrodes 15A through 15N and 16 shown here are connected to both the event detection sub-system 30 and the stimulation sub-system 40, it should be apparent that a separate set of electrodes and associated wires could be used with each sub-system. Furthermore, it is envisioned that any one or more of the electrodes 15A through 15N could be electrically connected (i.e., shorted) to the electrode 16 or to each other. This would be accomplished by appropriate switching circuitry in the stimulation sub-system 40.

The event detection sub-system 30 receives the EEG signals 21A through 21N (referenced to a system ground 19 connected to the wire 18 from the common electrode 16) and processes them to identify neurological events such as an epileptic seizure or its precursor. A central processing system 50 with a central processor 51 and memory 55 acts to control and coordinate all functions of the implantable system 10. A first interconnection 52 is used to transmit programming parameters and instructions to the event detection sub-system 30 from the central processing system 50. A second interconnection 53 is used to transmit signals to the central processing system 50 identifying the detection of a neurological event by the event detection sub-system 30. The second interconnection 53 is also used to transmit EEG and other related data for storage in the memory 55.

When an event is detected by the event detection sub-system 30 (by processing such as that disclosed and described in U.S. Pat. No. 6,016,449 to Fischell, et al., referenced above), the central processor 51 can command the stimulation sub-system 40 via a third interconnection 54 to transmit electrical signals to any one or more of the electrodes 15A through 15N via the wires 17A through 17N. It is anticipated that, if appropriate, electrical signals 412A to 412N, inclusive, are transmitted to certain locations in or near the brain, thereby aborting the normal progression of an epileptic seizure. It may also be necessary for the stimulation sub-system 40 to temporarily disable the event detection sub-system 30 via a fourth interconnection 29 when stimulation is imminent so that the stimulation signals are not inadvertently interpreted as a neurological event by the event detection sub-system 30.

The stimulation sub-system 40 may also be engaged to perform continuous or periodic stimulation to the brain electrodes 15A through 15N, inclusive. In one embodiment of the invention, electrical stimulation from the stimulation sub-system 40 can include any of a wide range of frequencies from approximately 2 Hz to approximately 200 Hz. Details of a signal generator capable of generating waveforms over such a frequency range are well known in the art of electronics design. In connection with the invention, it is, however, highly desirable to use stimulation at frequencies below 10 Hz. In particular, 5 Hz stimulation has been shown to be inhibitory to ictal spikes in cat brains, and it is believed to be similarly effective in human patients. It is also known to be less likely for low frequency stimulation to induce epileptiform activity.

In one embodiment of the invention, the low-frequency stimulation applied by an apparatus according to the invention comprises a substantially sinusoidal waveform having little or no energy in higher-frequency harmonics.

A power supply 90 provides power to each component of the system 10. Power supplies for comparable implantable devices such as heart pacemakers and heart defibrillators are well known in the art of implantable electronic devices. Such a power supply typically utilizes a primary (non-rechargeable) storage battery with an associated d-c to d-c converter to obtain any voltages required for the implantable system 10. However, it should be understood that in an alternative embodiment of the invention, the power supply could use a rechargeable battery that is charged by means of a coil of wire in the control module 20 that receives energy by magnetic induction from an external coil that is placed outside the patient but in close proximity to the control module 20. The implanted coil of wire could also be located remotely from control module 20 but joined to it by electrical wires. Such technology is well known from the rechargeable cardiac pacemaker. Furthermore, the same pair of coils of wire could be used to provide power to the implanted system 10 when it is desired to read out stored telemetry or reprogram some portion of the implanted system 10.

The central processing system 50 is connected to a data communication sub-system 60, thereby allowing data stored in the memory 55 to be retrieved by the patient's physician via a wireless communication link 72. An external data interface 70 can be directly connected to the physician's workstation 80 via a traditional serial data connection 74 (such as an RS-232 interface). Alternately, the serial connection may be made trans-telephonically, via modems 85 and 750 and a phone line 75 from the patient's home to the physician's workstation 80. Software in the computer section of the physician's workstation 80 allows the physician to read out a history of events detected by the implantable system 10, including EEG information before, during and after each event, as well as specific information relating to the detection of the event, such as the time evolving energy spectrum of the patient's EEG. In a preferred embodiment of the invention, the physician's workstation 80 also allows the physician to specify or alter any programmable parameters of the implantable system 10.

As shown in FIGS. 1 and 2, a buzzer 95 connected to the central processor 51 via a link 92 can be used to notify the patient that a neurological event has occurred, the implanted system 10 is about to deliver stimulation, or that the implanted system 10 is not functioning properly. In alternative embodiments, the buzzer could provide a mechanical vibration (typically an acoustic signal) or an electrical stimulation "tickle," either of which could be perceived by the patient. By placing the buzzer 95 near the ear and on the top of, below, or within a burr hole in the cranium, an acoustic signal emitted by the buzzer 95 would be transmitted via bone conduction and detectable by the patient's ear. This sound by itself can be an automatic means for stopping an epileptic seizure.

A real time clock 91 is used for timing and synchronizing various portions of the implanted system 10 and also to enable the system to provide the exact date and time corresponding to each neurological event that is detected by the implantable system 10 and recorded in the memory 55. A fifth interconnection 96 is used to send data from the central processor 51 to the real time clock 91 in order to set the correct date and time in the clock 91.

The various interconnections between sub-systems (e.g., the illustrated interconnections 29, 52, 53, 54, 56, 57, 92, 93 and 96) may be either analog or digital, single wire or multiple wires (a "data bus").

In an embodiment of the invention, the operation of the system 10 of FIG. 2 for detecting and treating a neurological event such as an epileptic seizure would typically be as follows:

1. The event detection sub-system 30 continuously processes the EEG signals 21A through 21N carried by the wires 17A through 17N from the N electrodes 15A through 15N.

2. When an event is detected, the event detection subsystem 30 notifies the central processor 51 via the second interconnection 53 that an event has occurred.

3. The central processor 51 then triggers the stimulation sub-system 40 via the third interconnection 54 to electrically stimulate the patient's brain with low frequency electrical signals in order to stop the neurological event, using any one, several or all of the electrodes 15A through 15N.

4. The stimulation sub-system 40 also sends a signal via the fourth interconnection 29 to the event detection sub-system 30 to disable event detection during stimulation to avoid an undesired input into the event detection sub-system 30.

5. The central processor system 50 will store EEG signals and event related data received from the event detection sub-system 30 via the second interconnection 53 over a time from X minutes before the event to Y minutes after the event for later analysis by the patient's physician. The value of X and Y may be set from as little as approximately 0.1 minutes to as long as approximately 30 minutes.

6. The central processor 51 may generate a "buzz" to notify the patient that an event has occurred by sending a signal via the link 92 to the buzzer 95.

Figure 3:
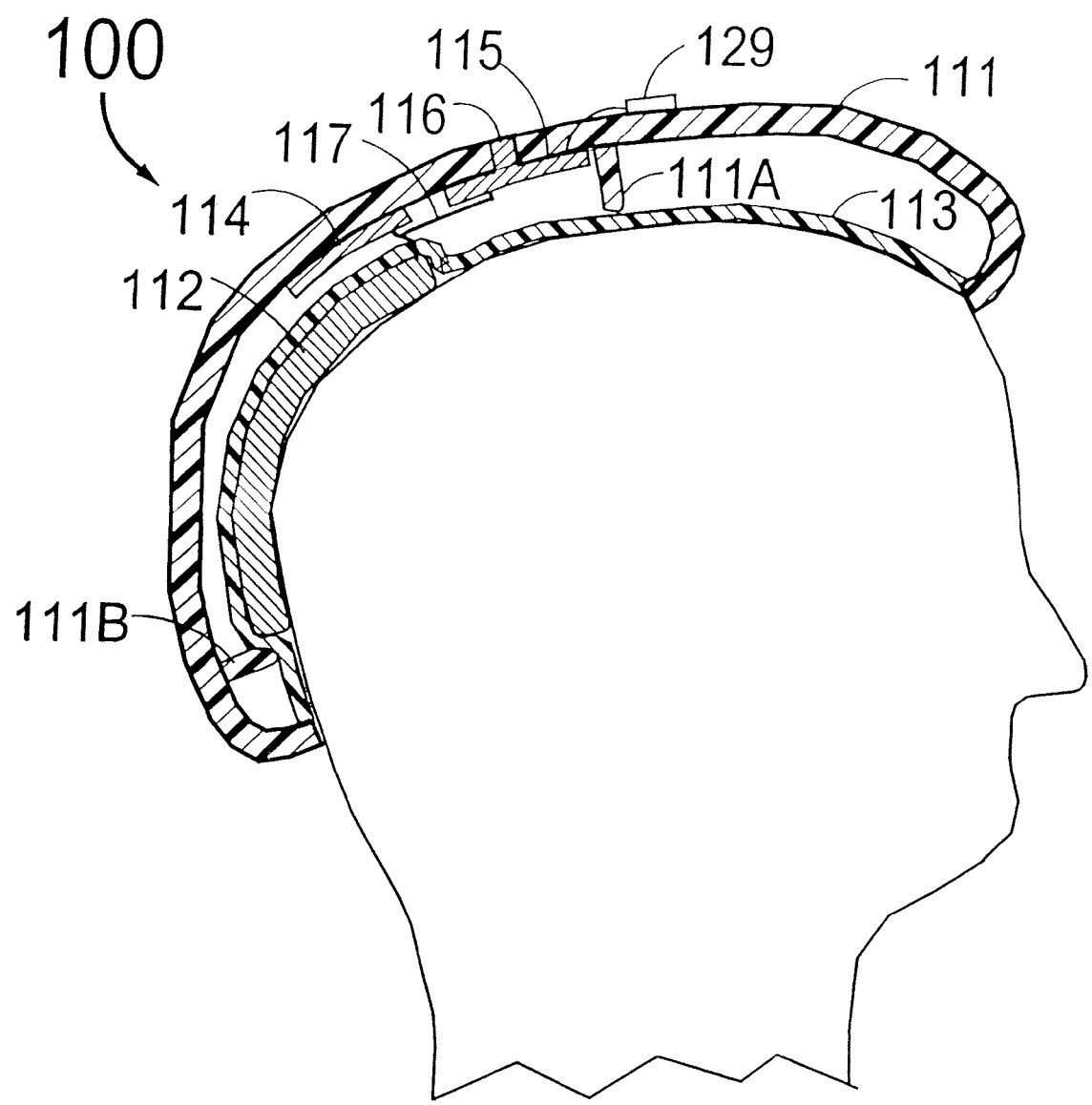
FIG. 3 is a cross section of an embodiment of the present invention showing a magnetic depolarizer system within a helmet on the head of a patient.

An alternative embodiment of the invention is shown in FIG. 3, which illustrates the head of a patient showing a cross section of a non-invasive transcranial magnetic depolarizer system 100 as it would be contained within a helmet 111 of the type used by bicycle riders. The magnetic depolarizer system 100 consists of a magnetic depolarizer coil assembly 112, a battery 114, electronic circuitry 115, a recharging receptacle 116 and interconnecting wires 117. The magnetic depolarizer system 100 is contained within the helmet 111 by means of an elastic support 113 that passes between a front support 111A and a rear support 111B. The purpose of the elastic support 113 is to keep the magnetic depolarizer coil 112 in comparatively tight contact with the patient's head and at specific location relative to the patient's cerebral cortex.

Figure 4A:
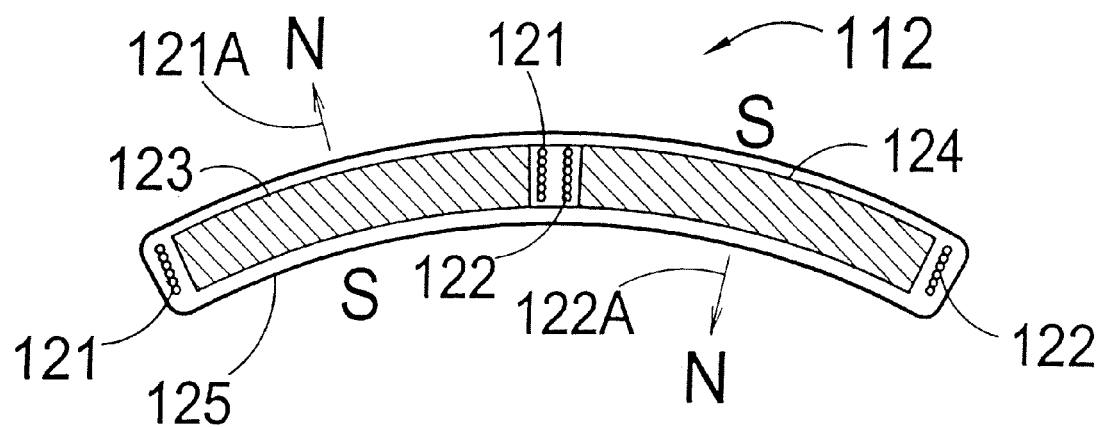
FIG. 4A is a longitudinal cross section of the magnetic depolarizer.

FIG. 4A is a longitudinal cross section of the magnetic depolarizer 112 of FIG. 3. The magnetic depolarizer coil assembly 112 consists of a first coil 121 placed into a figure-eight configuration with a second coil 122. The two coils 121 and 122 are electrically connected in series in such a way as to create north magnetic poles 121A and 122A in essentially opposite directions when electric current is flowing through the coils 121 and 122. This orientation of coils 121 and 122 can produce a comparatively strong magnetic field onto the cortex of the brain for a distance of a few centimeters beneath the cranium. If the magnetic field changes rapidly in time, it produces an electric current in the brain that can cause excited neurons to be depolarized. Ideally, slow TMS, at 1 to 5 Hz, will transiently depress excitability. In an embodiment of the invention, the intensity of the magnetic field at the surface of the brain should be between 0.1 and 10 Tesla. It is therefore an object of the present invention to use a device such as shown in FIG. 3 pulsed at a slow rate such as 1 or 2 Hz as an external means for treating a neurological disorder; preferably, this frequency is set and evaluated by the patient's physician. Such a device could be worn all the time for chronic epileptics where periodic slow stimulation would act to keep the focal region in a depressed condition, thus preventing a hyperexcited state associated with an epileptic seizure. For patients exhibiting an aura, the helmet could be put on as needed.

It should also be understood that the patient could use on or more elastic bands (without a helmet) to place the magnetic depolarizer coil assembly 112 at an appropriate location onto his or her head.

Figure 4B:
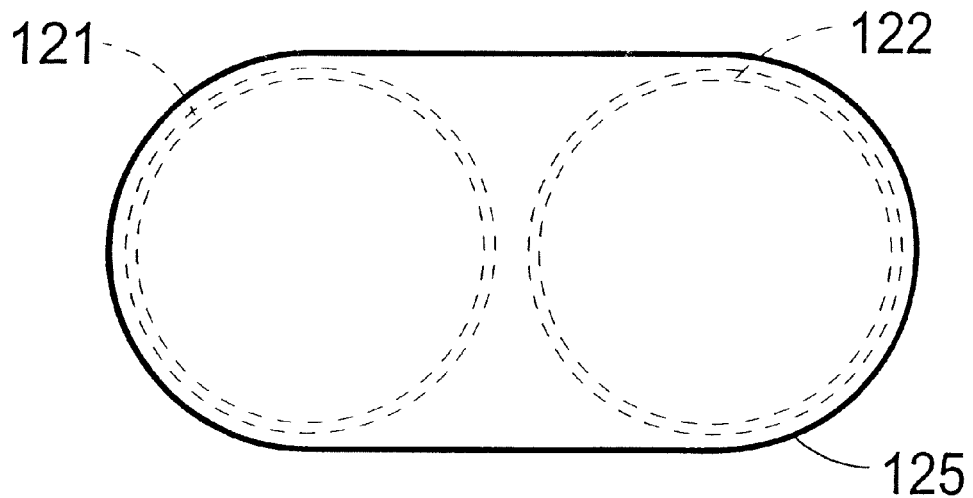
FIG. 4B is a top view of the magnetic depolarizer.

FIG. 4B is a top view of the magnetic depolarizer coil assembly 112 showing as dotted lines the outline of the coils 121 and 122. In both FIGS. 3A and 3B, it is shown that the coils 121 and 122 could be encapsulated into a plastic housing 125. Furthermore, FIG. 3A shows a magnetic core 123 in the coil 121 and a separate magnetic core 124 in the coil 122. These cores 123 and 124 are not required for the device to perform its intended purpose of generating a depolarizing electric current within the cerebral cortex, but their presence facilitates the generation of a high-intensity magnetic field in the brain at a lower level of electric current in the coils 121 and 122. To be effective at the high frequency of the magnetic pulses that are used to stimulate the cortex, the cores 123 and 124 would typically be formed from powdered iron or equivalent ferromagnetic material that has low eddy current and hysteresis losses.

Although FIGS. 4A and 4B show a race-track, figure eight type of design for the magnetic depolarizer coil assembly 112, it should be understood that a simple cylindrical coil (and other shaped coils as well) with or without a ferromagnetic core could be used to generate the desired time-varying magnetic field.

Figure 5:
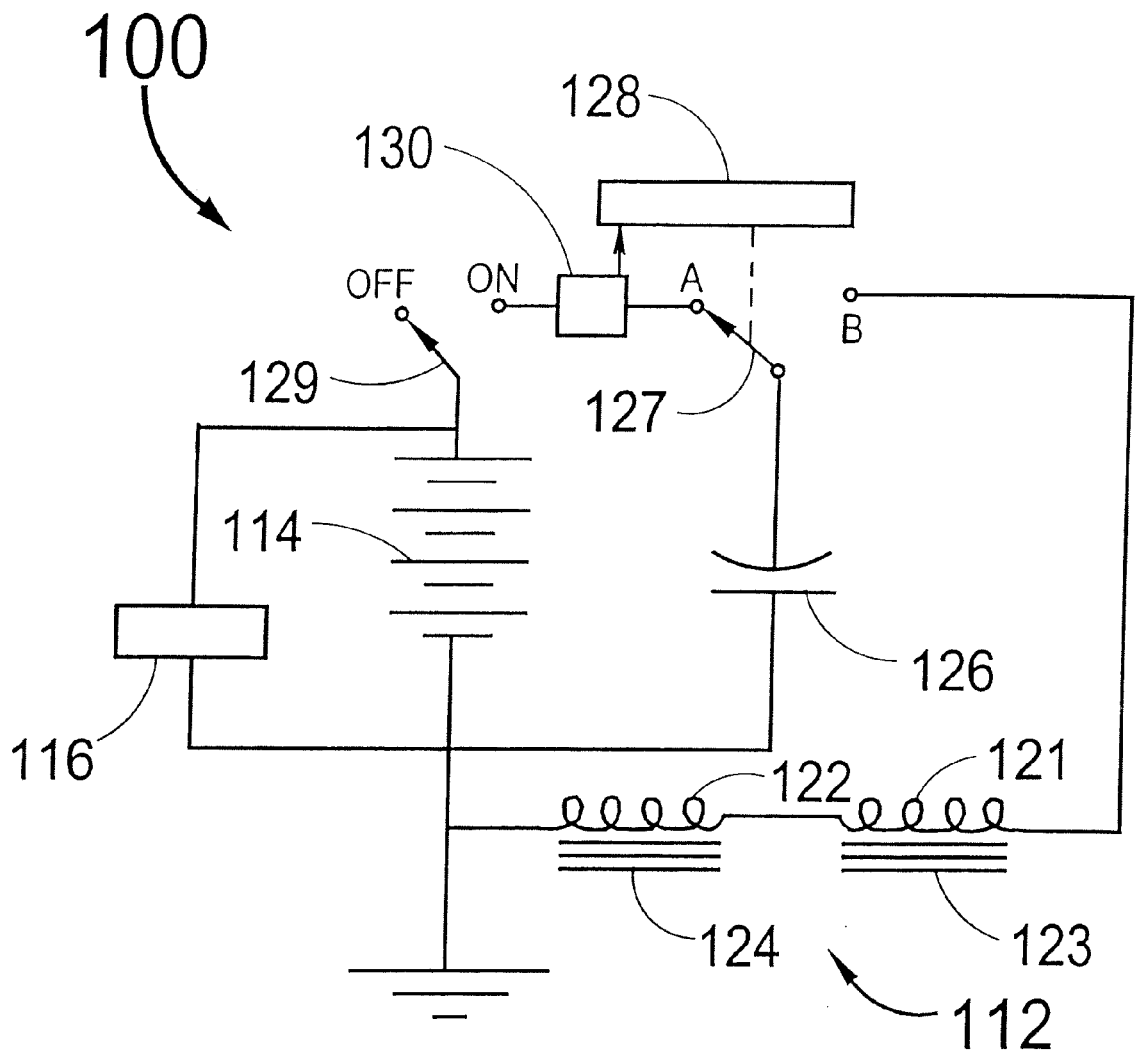
FIG. 5 is a simplified circuit diagram of the main components of a magnetic depolarizer system.

FIG. 5 is a simplified electrical diagram of the magnetic depolarizer system 100. The rechargeable battery 114 can be recharged through the receptacle 116 by receiving a plug from a conventional AC adapter (not shown) that connects to a-c line voltage (e.g., 115 volts) and delivers an appropriate d-c voltage to recharge the rechargeable battery 114. When the patient is experiencing an aura of a migraine headache or other symptoms of a neurological disorder, he or she can throw the ON-OFF switch 129 to the ON position. That would cause the d-c to d-c converter 130 to activate and generate a high voltage for rapidly charging the capacitor 126. When the control circuitry 128 senses that the appropriate voltage has been reached, it moves the switch 127 from position A to position B thus discharging the capacitor 126 through the coils 121 and 122 of the magnetic depolarizer 112. As previously described, the coils 121 and 122 could have air cores or they could use magnetically permeable cores 123 and 124. The control circuitry 128 can be used to set the repetition rate for causing magnetic pulses to be delivered. For example, a pulse from the capacitor might last for 70 microseconds and could be repeated at the slow frequency rates between approximately 0.1 and 10 Hz. A frequency of 1 Hz has been shown to be effective in depolarizing brain neurons and may be ideal for some patients. However, other patients might find other repetition rates to be more effective. It is even possible that a single magnetic pulse having a time duration between 10 and 1,000 microseconds could be used to stop an aura, thereby preventing the occurrence of a neurological event.

In an embodiment of the invention, the TMS administered through a non-invasive magnetic depolarizer system according to the invention comprises a low-frequency signal (between approximately 0.1 Hz and 10 Hz) modulated, via amplitude modulation or frequency modulation, onto a carrier frequency on the order of 100 Hz. It should be recognized that the carrier frequency given here is considered representative of a beneficial and advantageous carrier signal, and that various other carrier frequencies and modulation schemes are possible. Various waveforms are also possible for both the TMS waveform and the carrier waveform, including the substantially sinusoidal wave described above. Circuits capable of generating such stimulus signals are well known to practitioners skilled in the art of electronic circuit design.

Although FIGS. 3 and 5 show a battery operated magnetic depolarizer system 100, the system 100 could be operated by plugging into a receptacle at (typically) 115 or 230 volts a-c. Such a system might or might not use a battery as part of its circuitry.

Additional objects and advantages of the present invention will become apparent to those skilled in the art to which this invention relates from the subsequent description of the preferred embodiments and the appended claims, taken in conjunction with the accompanying drawings.

What is claimed is:

1. A readily portable magnetic depolarizer adapted to be positioned on the head of a patient comprising:
   at least one magnetic coil; and
   control circuitry in operable communication with the at least one magnetic coil, the control circuitry configured to generate a high-intensity magnetic field in the at least one magnetic coil for a duration of about 10 microseconds and 1000 microseconds;
   wherein the generated high-intensity magnetic field is provided by a carrier frequency having a low-frequency signal less than 10 Hz modulated thereon.

2. The readily portable magnetic depolarizer of claim 1 wherein the intensity of the magnetic field corresponding to the generated high-intensity magnetic field is between about 0.1 and 10 Tesla at a surface of the patient's brain.

3. The depolarizer of claim 1, wherein the low-frequency signal is modulated using one of frequency modulation and amplitude modulation.

4. The depolarizer of claim 1, wherein the carrier frequency is on the order of 100 Hz.

5. A method of delivering magnetic stimulation to the brain of a patient transcranially comprising:
   configuring control circuitry associated with at least one magnetic coil to cause the at least one magnetic coil to generate a high-intensity magnetic field that corresponds to a pulse of a duration of between about 10 microseconds and 1000 microseconds and an intensity of between about 0.1 and 10 Tesla using at least one magnetic coil to deliver at least one pulse corresponding to a high-intensity magnetic field when control circuitry associated with the at least one magnetic coil causes the high-intensity magnetic field to be generated,
   wherein the control circuitry further is configured to generate a plurality of high-intensity magnetic fields via a carrier frequency having a low-frequency signal between approximately 0.1 Hz and 10 Hz modulated thereon.

6. The method of claim 5, wherein the low-frequency signal is modulated using one of frequency modulation and amplitude modulation.

7. The method of claim 5, wherein the carrier frequency is on the order of 100 Hz.

* * * * *